United States Patent
Bambot et al.

[11] Patent Number: 6,055,451
[45] Date of Patent: Apr. 25, 2000

[54] APPARATUS AND METHOD FOR DETERMINING TISSUE CHARACTERISTICS

[75] Inventors: Shabbir Bambot, Suwanee; Mark L. Faupel, Alphretta, both of Ga.

[73] Assignee: SpectRx, Inc., Norcross, Ga.

[21] Appl. No.: 08/990,069

[22] Filed: Dec. 12, 1997

[51] Int. Cl.[7] .................................................. A61B 6/00
[52] U.S. Cl. .................. 600/476; 250/341.3; 250/461.2; 356/369
[58] Field of Search .................... 600/407, 473, 600/476, 478, 342, 343, 475, 310; 250/341.3, 461.2; 356/369; 606/10

[56] References Cited

U.S. PATENT DOCUMENTS

| | | | |
|---|---|---|---|
| 3,494,354 | 2/1970 | Yokota et al. | 128/6 |
| 4,056,724 | 11/1977 | Harte | 250/328 |
| 4,071,020 | 1/1978 | Pugliese | 128/2 |
| 4,084,905 | 4/1978 | Schreiber et al. | 356/85 |
| 4,099,872 | 7/1978 | White | 356/85 |
| 4,115,699 | 9/1978 | Mizuta et al. | 250/461 |
| 4,122,348 | 10/1978 | Bruck | 250/461 |
| 4,125,828 | 11/1978 | Resnick et al. | 340/146.3 |
| 4,127,773 | 11/1978 | West | 250/461 |
| 4,131,800 | 12/1978 | Bruck et al. | 250/461 |
| 4,144,456 | 3/1979 | Harte | 250/302 |
| 4,160,016 | 7/1979 | Ullman | 424/8 |
| 4,161,515 | 7/1979 | Ullman | 424/8 |
| 4,162,405 | 7/1979 | Chance et al. | 250/461 |
| 4,203,670 | 5/1980 | Bromberg | 356/367 |
| 4,223,680 | 9/1980 | Jobsis | 128/633 |
| 4,236,526 | 12/1980 | Richard | 128/633 |
| 4,266,549 | 5/1981 | Kimura | 128/303.1 |
| 4,330,207 | 5/1982 | Nogami et al. | 356/318 |
| 4,407,964 | 10/1983 | Elings et al. | 436/518 |
| 4,449,535 | 5/1984 | Renault | 128/634 |
| 4,501,970 | 2/1985 | Nelson | 250/458.1 |
| 4,516,856 | 5/1985 | Popelka | 356/368 |
| 4,531,834 | 7/1985 | Nogami | 356/73 |
| 4,541,438 | 9/1985 | Parker et al. | 128/664 |
| 4,556,057 | 12/1985 | Hiruma et al. | 128/303.1 |
| 4,577,110 | 3/1986 | MacBride et al. | 250/461.2 |
| 4,600,306 | 7/1986 | Hara et al. | 356/317 |
| 4,632,550 | 12/1986 | Hara et al. | 356/311 |
| 4,643,877 | 2/1987 | Opitz et al. | 422/68 |
| 4,661,711 | 4/1987 | Harjunmaa | 250/458.1 |
| 4,675,529 | 6/1987 | Kushida | 250/458.1 |
| 4,681,859 | 7/1987 | Kramer | 436/501 |
| 4,682,594 | 7/1987 | Mok | 128/303.1 |

(List continued on next page.)

*Primary Examiner*—Marvin M. Lateef
*Assistant Examiner*—Shawna J Shaw
*Attorney, Agent, or Firm*—Fleshner & Kim

[57] ABSTRACT

An apparatus and method embodying the invention include utilizing a device intended to be inserted into a patient's body to determine a characteristic of a target tissue. In one apparatus and method, a device illuminates the target tissue with amplitude modulated excitation electromagnetic radiation, and the device senses a returned electromagnetic radiation. A phase shift between the excitation and return electromagnetic radiation is determined, and the phase shift is used to determine characteristics of the target tissue. A demodulation factor, representing ratios of the AC and DC components of the excitation and return electromagnetic radiation may also be calculated and used to determine characteristics of the target tissue. In another apparatus and method embodying the invention, a device illuminates a target tissue with polarized electromagnetic radiation, and a return electromagnetic radiation is sensed. The amplitude of the returned electromagnetic radiation is sensed in mutually perpendicular planes, and this information is used to determine an anisotropy factor. The anisotropy factor, in turn, is used to determine characteristics of the target tissue. In either of the above-described methods, the return radiation could be a portion of the excitation radiation that has been reflected or scattered from the target tissue, or the returned electromagnetic radiation could be fluorescent emissions generated by endogenous or exogenous fluorophores located in the target tissue.

48 Claims, 6 Drawing Sheets

U.S. PATENT DOCUMENTS

| | | | |
|---|---|---|---|
| 4,686,371 | 8/1987 | Birch et al. | 250/461.1 |
| 4,718,417 | 1/1988 | Kittrell et al. | 128/303.1 |
| 4,722,607 | 2/1988 | Anselment et al. | 356/417 |
| 4,751,190 | 6/1988 | Chiapetta et al. | 436/546 |
| 4,753,530 | 6/1988 | Knight et al. | 356/73 |
| 4,755,684 | 7/1988 | Leiner et al. | 250/461.1 |
| 4,758,727 | 7/1988 | Tomei et al. | 250/458.1 |
| 4,768,513 | 9/1988 | Suzuki | 128/634 |
| 4,785,806 | 11/1988 | Deckelbaum | 128/303.1 |
| 4,786,170 | 11/1988 | Groebler | 356/318 |
| 4,786,813 | 11/1988 | Svanberg et al. | 250/461.1 |
| 4,828,984 | 5/1989 | Schwartz | 435/7 |
| 4,833,332 | 5/1989 | Robertson, Jr. et al. | 250/458.1 |
| 4,840,485 | 6/1989 | Gratton | 356/317 |
| 4,852,579 | 8/1989 | Gilstad et al. | 128/665 |
| 4,855,930 | 8/1989 | Chao et al. | 364/497 |
| 4,877,583 | 10/1989 | Miwa et al. | 422/73 |
| 4,877,965 | 10/1989 | Dandliker et al. | 250/458.1 |
| 4,894,547 | 1/1990 | Leffell et al. | 250/461.2 |
| 4,895,156 | 1/1990 | Schulze | 128/634 |
| 4,913,142 | 4/1990 | Kittrell et al. | 606/7 |
| 4,925,804 | 5/1990 | Hale et al. | 436/501 |
| 4,930,516 | 6/1990 | Alfano et al. | 128/665 |
| 4,937,457 | 6/1990 | Mitchell | 250/458.1 |
| 4,947,850 | 8/1990 | Vanderkooi et al. | |
| 4,957,114 | 9/1990 | Zeng et al. | 128/665 |
| 4,972,331 | 11/1990 | Chance | 364/550 |
| 4,973,848 | 11/1990 | Kolobanov et al. | 250/458.1 |
| 4,981,138 | 1/1991 | Deckelbaum et al. | 128/665 |
| 5,003,977 | 4/1991 | Suzuki et al. | 128/633 |
| 5,014,707 | 5/1991 | Schwarz et al. | 128/633 |
| 5,021,661 | 6/1991 | Masutani | 250/339 |
| 5,022,757 | 6/1991 | Modell | 356/318 |
| 5,030,832 | 7/1991 | Williams et al. | 250/458.1 |
| 5,034,010 | 7/1991 | Kittrell et al. | 606/15 |
| 5,039,219 | 8/1991 | James et al. | 356/318 |
| 5,042,494 | 8/1991 | Alfano | 128/665 |
| 5,043,585 | 8/1991 | Fehrenbach et al. | 250/458.1 |
| 5,053,626 | 10/1991 | Tillotson | 259/458.1 |
| 5,061,075 | 10/1991 | Alfano et al. | 356/417 |
| 5,061,076 | 10/1991 | Hurley | 356/417 |
| 5,062,431 | 11/1991 | Potter | 128/665 |
| 5,092,331 | 3/1992 | Nakamura et al. | 128/634 |
| 5,104,392 | 4/1992 | Kittrell et al. | 606/15 |
| 5,106,387 | 4/1992 | Kittrell et al. | 606/15 |
| 5,111,821 | 5/1992 | Potter | 128/665 |
| 5,115,137 | 5/1992 | Andersson-Engls et al. | 250/461.2 |
| 5,119,815 | 6/1992 | Chance | 128/633 |
| 5,122,974 | 6/1992 | Chance | 364/550 |
| 5,125,404 | 6/1992 | Kittrell et al. | 128/634 |
| 5,127,405 | 7/1992 | Alcala et al. | 128/633 |
| 5,131,398 | 7/1992 | Alfano et al. | 128/665 |
| 5,143,066 | 9/1992 | Komives et al. | 128/634 |
| 5,151,869 | 9/1992 | Alcala | 364/497 |
| 5,168,162 | 12/1992 | Oong et al. | |
| 5,187,672 | 2/1993 | Chance et al. | 364/550 |
| 5,196,709 | 3/1993 | Berndt et al. | 250/458.1 |
| 5,201,318 | 4/1993 | Rava et al. | 128/665 |
| 5,205,291 | 4/1993 | Potter | 128/654 |
| 5,212,099 | 5/1993 | Marcus | 436/172 |
| 5,213,105 | 5/1993 | Gratton et al. | 128/664 |
| 5,257,202 | 10/1993 | Feddersen et al. | 364/498 |
| 5,261,410 | 11/1993 | Alfano et al. | 128/664 |
| 5,290,275 | 3/1994 | Kittrell et al. | 606/15 |
| 5,293,872 | 3/1994 | Alfano et al. | 128/664 |
| 5,303,026 | 4/1994 | Strobl et al. | 356/318 |
| 5,304,173 | 4/1994 | Kittrell et al. | 606/15 |
| 5,315,993 | 5/1994 | Alcala | 128/634 |
| 5,318,023 | 6/1994 | Vari et al. | 128/633 |
| 5,318,024 | 6/1994 | Kittrell et al. | 128/634 |
| 5,323,008 | 6/1994 | Studholme et al. | 250/458.1 |
| 5,329,353 | 7/1994 | Ichimura et al. | 356/328 |
| 5,332,905 | 7/1994 | Brooker et al. | 250/458.1 |
| 5,340,716 | 8/1994 | Ullman et al. | 435/6 |
| 5,345,941 | 9/1994 | Rava et al. | 128/665 |
| 5,348,018 | 9/1994 | Alfano et al. | 128/665 |
| 5,348,890 | 9/1994 | Ichikawa et al. | 436/172 |
| 5,349,954 | 9/1994 | Tiemann et al. | 128/634 |
| 5,353,799 | 10/1994 | Chance | 128/664 |
| 5,363,854 | 11/1994 | Martens et al. | 128/665 |
| 5,369,496 | 11/1994 | Alfano et al. | 356/446 |
| 5,370,119 | 12/1994 | Mordon et al. | 128/654 |
| 5,377,676 | 1/1995 | Vari et al. | 128/634 |
| 5,383,467 | 1/1995 | Auer et al. | 128/664 |
| 5,386,827 | 2/1995 | Chance et al. | 128/633 |
| 5,395,752 | 3/1995 | Law et al. | 435/6 |
| 5,402,778 | 4/1995 | Chance | 128/633 |
| 5,408,996 | 4/1995 | Salb | 128/633 |
| 5,413,108 | 5/1995 | Alfano | 128/665 |
| 5,419,323 | 5/1995 | Kittrell et al. | 128/653.1 |
| 5,421,337 | 6/1995 | Richards-Kortum et al. | 128/665 |
| 5,421,339 | 6/1995 | Ramanujam et al. | 128/665 |
| 5,422,719 | 6/1995 | Goldstein | 356/318 |
| 5,435,307 | 7/1995 | Friauf et al. | 128/633 |
| 5,439,000 | 8/1995 | Gunderson et al. | 128/664 |
| 5,452,723 | 9/1995 | Wu et al. | 128/664 |
| 5,459,323 | 10/1995 | Morgan | 250/458.1 |
| 5,460,971 | 10/1995 | Gottlieb | 436/68 |
| 5,467,767 | 11/1995 | Alfano et al. | 128/665 |
| 5,474,910 | 12/1995 | Alfano | 435/34 |
| 5,480,775 | 1/1996 | Ito et al. | 435/7.2 |
| 5,485,530 | 1/1996 | Lakowicz et al. | 382/191 |
| 5,491,343 | 2/1996 | Brooker | 250/458.1 |
| 5,492,118 | 2/1996 | Gratton et al. | 128/633 |
| 5,497,769 | 3/1996 | Gratton et al. | 128/633 |
| 5,500,536 | 3/1996 | Nogami et al. | 250/458.1 |
| 5,504,336 | 4/1996 | Noguchi | 250/458.1 |
| 5,507,287 | 4/1996 | Palcic et al. | 128/633 |
| 5,515,864 | 5/1996 | Zuckerman | 128/633 |
| 5,517,313 | 5/1996 | Colvin, Jr. | 356/417 |
| 5,533,508 | 7/1996 | Doiron | 128/634 |
| 5,548,124 | 8/1996 | Takeshima et al. | 250/458.1 |
| 5,553,614 | 9/1996 | Chance | 128/633 |
| 5,555,885 | 9/1996 | Chance | 128/654 |
| 5,557,415 | 9/1996 | Nielsen et al. | 356/417 |
| 5,562,100 | 10/1996 | Kittrell et al. | 128/665 |
| 5,564,417 | 10/1996 | Chance | 128/633 |
| 5,565,982 | 10/1996 | Lee et al. | 356/317 |
| 5,579,773 | 12/1996 | Vo-Dinh et al. | 128/665 |
| 5,582,168 | 12/1996 | Samuels et al. | |
| 5,590,660 | 1/1997 | MacAulay et al. | 128/664 |
| 5,596,987 | 1/1997 | Chance | 128/633 |
| 5,596,992 | 1/1997 | Haaland et al. | |
| 5,601,079 | 2/1997 | Wong et al. | 128/633 |
| 5,601,087 | 2/1997 | Gunderson et al. | 128/664 |
| 5,612,540 | 3/1997 | Richards-Kortum et al. | 250/461.2 |
| 5,623,932 | 4/1997 | Ramanujam et al. | 128/665 |
| 5,624,847 | 4/1997 | Lakowicz et al. | 436/68 |
| 5,626,134 | 5/1997 | Zuckerman | 128/633 |
| 5,628,310 | 5/1997 | Rao et al. | 128/633 |
| 5,635,402 | 6/1997 | Alfano et al. | 436/63 |
| 5,647,368 | 7/1997 | Zeng et al. | 128/665 |
| 5,664,574 | 9/1997 | Chance | 128/664 |
| 5,673,701 | 10/1997 | Chance | 128/664 |
| 5,678,550 | 10/1997 | Bassen et al. | |
| 5,683,888 | 11/1997 | Campbell | 435/8 |
| 5,687,730 | 11/1997 | Doiron et al. | 128/665 |
| 5,697,373 | 12/1997 | Richards-Kortum et al. | 128/664 |
| 5,699,795 | 12/1997 | Richards-Kortum et al. | 128/634 |
| 5,699,798 | 12/1997 | Hochman et al. | 128/653.1 |
| 5,701,902 | 12/1997 | Var et al. | 128/664 |
| 5,701,903 | 12/1997 | Sano et al. | 128/665 |
| 5,713,352 | 2/1998 | Essenpreis et al. | |
| 5,713,364 | 2/1998 | DeBaryshe et al. | |
| 5,722,406 | 3/1998 | Papaioannou | |
| 5,762,609 | 6/1998 | Benaron et al. | |
| 5,807,263 | 9/1998 | Chance | |

APPARATUS AND METHOD FOR DETERMINING TISSUE CHARACTERISTICS

BACKGROUND OF THE INVENTION

1. Field of the Invention

The invention is related to apparatus and methods for determining tissue characteristics within a body of a patient.

2. Background of the Related Art

It is known to irradiate a target tissue with electromagnetic radiation and to detect returned electromagnetic radiation to determine characteristics of the target tissue. In known methods, the amplitudes and wavelengths of the returned radiation are analyzed to determine characteristics of the target tissue. For instance, U.S. Pat. No. 4,718,417 to Kittrell et al. discloses a method for diagnosing the type of tissue within an artery, wherein a catheter is inserted into an artery and excitation light at particular wavelengths is used to illuminate the interior wall of the artery. Material or tissue within the artery wall emits fluorescent radiation in response to the excitation light. A detector detects the fluorescent radiation and analyzes the amplitudes and wavelengths of the emitted fluorescent radiation to determine whether the illuminated portion of the artery wall is normal, or covered with plaque. The contents of U.S. Pat. No. 4,718,417 are hereby incorporated by reference.

U.S. Pat. No. 4,930,516 to Alfano et al. discloses a method for detecting cancerous tissue, wherein a tissue sample is illuminated with excitation light at a first wavelength, and fluorescent radiation emitted in response to the excitation light is detected. The wavelength and amplitude of the emitted fluorescent radiation are then examined to determine whether the tissue sample is cancerous or normal. Normal tissue will typically have amplitude peaks at certain known wavelengths, whereas cancerous tissue will have amplitude peaks at different wavelengths. Alternatively the spectral amplitude of normal tissue will differ from cancerous tissue at the same wavelength. The disclosure of U.S. Pat. No. 4,930,516 is hereby incorporated by reference.

Still other patents, such as U.S. Pat. No. 5,369,496 to Alfano et al., disclose methods for determining characteristics of biological materials, wherein a target tissue is illuminated with light, and backscattered or reflected light is analyzed to determine the tissue characteristics. The contents of U.S. Pat. No. 5,369,496 are hereby incorporated by reference.

These methods rely on the information from steady state emissions to perform a diagnostic measurement. It is known that the accuracy of measurements made by these methods is limited by practical issues such as variation in lamp intensity and changes in fluorophore concentration. It is desirable to measure an intrinsic physical property to eliminate errors that can be caused by practical problems, to thereby make an absolute measurement with greater accuracy. One intrinsic physical property is the fluorescence lifetime or decay time of fluorophores being interrogated, the same fluorophores that serve as indicators of disease in tissue.

It is known to look at the decay time of fluorescent emissions to determine the type or condition of an illuminated tissue.

To date, apparatus for detection of the lifetime of fluorescent emissions have concentrated on directly measuring the lifetime of the fluorescent emissions. Typically, a very short burst of excitation light is directed at a target tissue, and fluorescent emissions from the target tissue are then sensed with a detector. The amplitude of the fluorescent emissions are recorded, over time, as the fluorescent emissions decay. The fluorescent emissions may be sensed at specific wavelengths, or over a range of wavelengths. The amplitude decay profile, as a function of time, is then examined to determine a property or condition of the target tissue.

For instance, U.S. Pat. No. 5,562,100 to Kittrell et al. discloses a method of determining tissue characteristics that includes illuminating a target tissue with a short pulse of excitation radiation at a particular wavelength, and detecting fluorescent radiation emitted by the target tissue in response to the excitation radiation. In this method, the amplitude of the emitted radiation is recorded, over time, as the emission decays. The amplitude profile is then used to determine characteristics of the target tissue. Similarly, U.S. Pat. No. 5,467,767 to Alfano et al. also discloses a method of determining whether a tissue sample includes cancerous cells, wherein the amplitude decay profile of fluorescent emissions are examined. The contents of U.S. Pat. Nos. 5,562,100 and 5,467,767 are hereby incorporated by reference.

Unfortunately, these methods require expensive components that are capable of generating extremely short bursts of excitation light, and that are capable of recording the relatively faint fluorescent emissions that occur over time. The high cost of these components has prevented these techniques from being used in typical clinical settings.

Other U.S. patents have explained that the decay time of fluorescent emissions can be indirectly measured utilizing phase shift or polar anisotropy measurements. For instance, U.S. Pat. No. 5,624,847 to Lakowicz et al. discloses a method for determining the presence or concentration of various substances using a phase shift method. U.S. Pat. No. 5,515,864 to Zuckerman discloses a method for measuring the concentration of oxygen in blood utilizing a polar anisotropy measurement technique. Each of these methods indirectly measure the lifetime of fluorescent emissions generated in response to excitation radiation. The contents of U.S. Pat. Nos. 5,624,847 and 5,515,864 are hereby incorporated by reference.

SUMMARY OF THE INVENTION

The invention encompasses apparatus and methods for determining characteristics of target tissues within a patient's body, wherein excitation electromagnetic radiation is used to illuminate a target tissue and electromagnetic radiation returned from the target tissue is analyzed to determine the characteristics of the target tissue. Some apparatus and methods embodying the invention can be used to perform a diagnosis at or slightly below the surface of a patient's tissues. For instance, methods and apparatus embodying the invention could be used to diagnose the condition of a patient's skin, the lining of natural body lumens such as the gastrointestinal tract, or the surfaces of body organs or blood vessels. Other apparatus and methods embodying the invention can be used to perform a diagnosis deep within a patient's body tissues where the excitation radiation has to pass through several centimeters of tissue before it interacts with the target tissue, such as in diagnosis of tumors and lesions deep in a patient's breast.

The returned electromagnetic radiation can comprise only fluorescent emissions from the target tissue that are caused by the excitation electromagnetic radiation. In this instance, apparatus or methods embodying the invention would measure the lifetime or decay time of the fluorescent emissions and use this information to determine characteristics of the target tissue. The fluorescent emissions may be generated by endogenous or exogenous fluorescent materials in the target tissue. Both phase shift and polar anisotropy techniques can be used to perform these types of measurements.

The returned electromagnetic radiation can also comprise a portion of the excitation electromagnetic radiation that is scattered or reflected from or transmitted through the target tissue. Analysis of the scattered, reflected or transmitted excitation radiation gives a measure of absorption and scattering characteristics of the target tissue. This information can be used by itself to provide a diagnosis, or the information can be used to calibrate the results of the fluorescent emission measurements to arrive at a more accurate measurement. The reflected or scattered excitation radiation can be measured using intensity based techniques, or phase shift techniques.

In phase shift techniques for measuring either reflected or scattered excitation radiation, or fluorescent emissions caused by the excitation radiation, the excitation electromagnetic radiation is amplitude modulated at a predetermined frequency. A detector that senses the returned radiation (either reflected/scattered excitation radiation or fluorescent emissions) is used to detect the amplitude and timing characteristics of the returned electromagnetic radiation. The excitation and returned radiation will have the same frequency, but the amplitude of the returned radiation should be smaller than the amplitude of the excitation radiation, and the returned radiation will be out of phase with the excitation radiation. The demodulation and phase shift between the excitation and returned electromagnetic radiation gives a measure of the characteristics of the target tissue. The demodulation amount can be represented by a demodulation factor, which is a ratio of the AC and DC amplitude components of the excitation and returned electromagnetic radiation.

A polar anisotropy technique may also be used to detect fluorescent emissions to obtain a measure of the decay time or lifetime of the fluorescent emissions. In the polar anisotropy techniques, the target tissue is illuminated with polarized excitation electromagnetic radiation. The returned fluorescent emissions are conveyed to a polarizing beam splitter that separates the returned electromagnetic radiation into two light beams that are polarized in mutually perpendicular planes. In a preferred embodiment, one plane is parallel to the polarization plane of the excitation radiation, and the second plane is perpendicular to that plane. Detectors detect the amplitudes of the two perpendicularly polarized beams of light. The detected amplitudes are used to calculate an anisotropy factor that is representative of the lifetime or decay time of the fluorescent emissions.

In either the phase shift or polar anisotropy techniques, the apparatus or method may only analyze returned radiation within certain predetermined wavelengths. Also, the apparatus and methods may only analyze fluorescent decays that occur for more than a predetermined period of time, or less than a predetermined period of time. This allows the device to distinguish between different types of tissues that have different fluorescent decay times.

Because of changes in the fluoroescent emissions of endogenous and exogenous fluorophores that occur within a patient's body, the above-described methods were not previously used for in vivo detection of cancerous or diseased tissues. Methods and apparatus embodying the present invention, however, allow for in vivo detection of diseased tissues using relatively simple and inexpensive instrumentation.

The above described techniques can be used to determine the conditions of multiple portions of a target tissue, and the determined conditions can be used to create a map of the target tissue. Such a map could then be either displayed on a display screen, or presented in hard copy format.

An instrument embodying present invention could be in the form of an endoscope designed to be introduced into natural lumen or a cavity of a patient's body. Alternatively, the instrument might be in the form of a catheter designed to be introduced into blood vessels of a patient's body. Regardless of whether the apparatus is in the form of an endoscope or a catheter, the apparatus could include means for delivering a therapeutic pulse of electromagnetic radiation to the target tissue. The device could also include means for delivering a therapeutic dose of medication to the target tissue. Further, the instrument could include means for sampling the target tissue depending upon the determined condition of the target tissue.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

Preferred embodiments of the present invention will now be described with reference to the following drawing figures, wherein like elements are referred to with like reference numerals, and wherein.

DETAILED DESCRIPTION OF PREFERRED EMBODIMENTS

The phase shift and polar anisotropy techniques that are the subject of the present invention are more simple and less expensive to implement than the known apparatus and techniques for detecting the lifetime or decay time of fluorescent emissions. As a result, they can be implemented for real world in vivo testing of target tissues.

It is known that when a fluorophore is excited with an infinitesimal pulse of light, the resulting fluorescent emission decays exponentially. The intensity of the fluorescent emission is given by Equation (1), where $I_i$ is the initial fluorescence intensity, t is the time, and $\tau$ is the fluorescence lifetime.

$$I(t) = I_i e^{-t/\tau} \qquad \text{Equation (1)}$$

If an excitation light is amplitude modulated at a constant frequency, instead of simply illuminating the target tissue with a short burst of light, the resulting fluorescence emissions will also appear to be amplitude modulated. The amplitude of the fluorescent emissions will be smaller than the amplitude of the excitation light, but the fluorescent emissions will have the same frequency. Also, there will be a phase shift between the excitation light and the fluorescent emissions.

Figure 1:
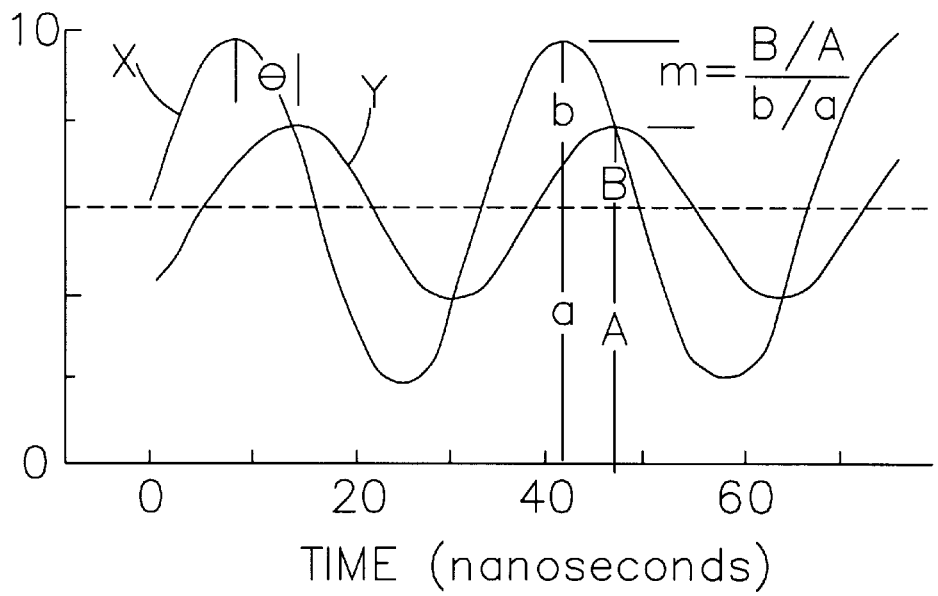
FIG. 1 is a chart showing the amplitudes and phase shift of excitation and returned electromagnetic radiation.

FIG. 1 illustrates the concept of illuminating a target tissue with amplitude modulated excitation electromagnetic radiation and sensing the resulting fluorescent emissions. In FIG. 1, the waveform X shows the amplitude of modulated excitation electromagnetic radiation from a source. The amplitude of returned fluorescent emissions is shown as waveform Y. As can be seen in FIG. 1, the peaks of the waveform Y are delayed, or phase shifted, relative to the peaks of waveform X by an amount θ. This is referred to as a phase shift amount.

In addition, the amplitude of the fluorescent emissions is smaller than the amplitude of the excitation light source. A demodulation factor m represents a ratio of the DC and AC components of the fluorescent emissions relative to the DC and AC components of the excitation electromagnetic radiation.

The Fourier transform of equation (1), yields Equation (2), shown below.

$$I(\omega) = I_t \tau / (1 - i\omega\tau) \quad \text{Equation (2)}$$

Equation (2), in turn, can be used to derive the phase shift and demodulation factor, as shown in Equations (3) and (4) below.

$$\theta_s = \tan^{-1}(\omega\tau) \quad \text{Equation (3)}$$

$$m = 1 \Big/ \sqrt{(1 + \omega^2 \tau^2)} \quad \text{Equation (4)}$$

An apparatus for in vivo determination of the characteristics of a target tissue utilizing a phase shift technique will now be described with reference to FIGS. 1 and 2.

Figure 2:
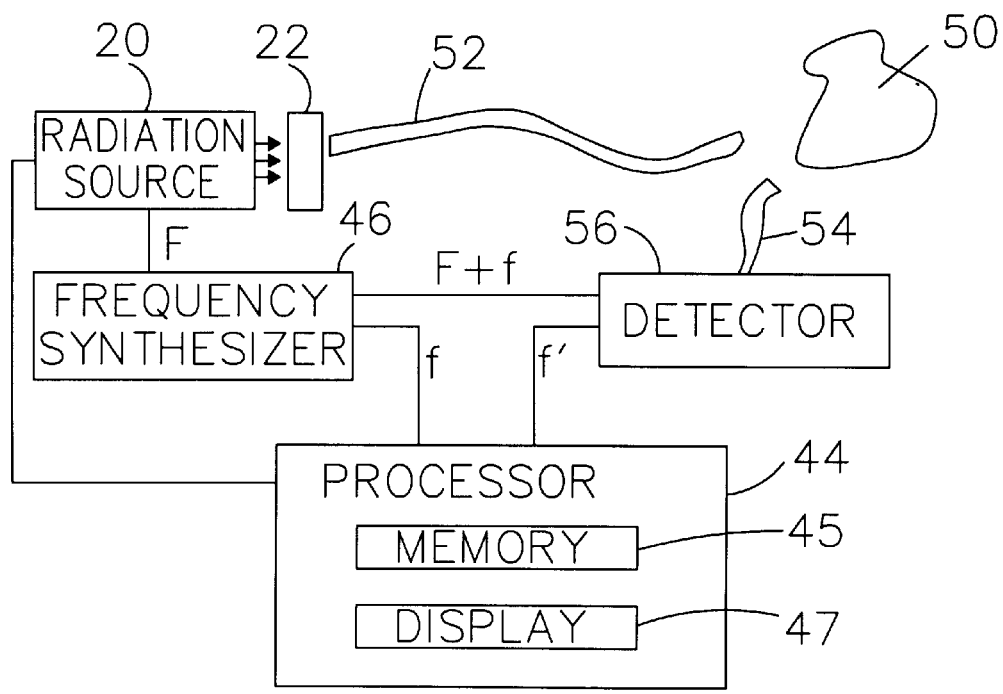
FIG. 2 is a diagram showing an apparatus embodying the invention capable of performing a phase shift measurement.

A diagram of an apparatus embodying the invention is shown in FIG. 2. The apparatus includes a source 20 of electromagnetic radiation, which is connected to a frequency synthesizer 46. The radiation source 20 produces electromagnetic radiation that is conducted to a target tissue 50. The radiation may be conducted to the target tissue 50 through one or more emission optical fibers 52. The apparatus may also include a filter 22 for controlling the electromagnetic radiation emitted from the radiation source 20. The radiation source could comprise a laser, a light emitting diode, a fluorescent tube, an incandescent bulb, or any other type of device that is capable of emitting electromagnetic radiation, as is well known to those skilled in the art.

Electromagnetic radiation returned from target tissue 50, is sensed by a detector 56. The returned electromagnetic radiation could comprise either a portion of the excitation electromagnetic radiation that is scattered or reflected from the target tissue, or fluorescent emissions from fluorophores in the target tissue that have been excited by the excitation radiation. The detector may comprise a photomultiplier tube, a photosensitive diode, a charge coupled device, or any other type of electromagnetic radiation sensor, as is also well known to those skilled in the art.

If the detector is a small charge coupled device, it could be located at a distal end of an endoscope or catheter instrument. In this instance, the charge coupled device would already be located adjacent the target tissue such that the detector could directly sense the return radiation. The charge coupled device would then need some means for communicating its information to a processor 44.

If the detector is not a charge coupled device located at a distal end of an instrument, the returned electromagnetic radiation may be conducted to the detector 56 through one or more return optical fibers 54. The return optical fibers 54 and the excitation optical fibers 52 may be co-located within the same instrument, or they may be located in separate instruments. Alternately, the same optical fibers within an instrument may be used to perform both excitation and return functions.

The frequency synthesizer 46 is a combination of two high frequency synthesizers that are preferably phase locked. The frequency synthesizer outputs three signals. The first signal has a frequency F, the second signal has a frequency of F+f, which is a slightly in frequency than the signal F, and the third signal has a frequency f, which is lower in frequency than the first two signals. The excitation radiation from the radiation source 20, which illuminates the target tissue 50, is amplitude modulated at the high frequency F. The signal F+f drives the detector 56. Finally, the low frequency signal f, which is readily derived as the difference between the two high frequency signals, is sent as a reference signal to the processor 44.

The embodiment shown in FIG. 2, is a heterodyne system. The detector 56 senses the returned radiation and generates a signal that is modulated at the same frequency as the excitation radiation, or the frequency F. The detector 56 then uses the higher frequency signal F+f to convert the signal corresponding to the returned radiation into a low difference frequency signal f', which includes information on the returned radiation signal. The low frequency signal f' is then compared to the low frequency signal f, which was generated by the frequency synthesizer 46, to calculate a phase shift θ and demodulation factor m. Other types of heterodyne systems could also be used.

The processor device 44 may include a memory 45 and a display 47. In fact, the processor device may comprise a typical personal computer. The processor 44 may also be configured to determine the AC and DC components of the amplitudes of the excitation and returned electromagnetic radiation signals. The processor may also be configured to calculate a demodulation factor m. As shown in FIG. 1, the demodulation factor m represents a ratio of the AC component B divided by the DC component A of the returned electromagnetic radiation to the AC component b divided by the DC component a of the excitation electromagnetic radiation. The demodulation factor can be used in conjunction with the phase difference φ to more accurately determine characteristics of the target tissue.

If the detector 56 is measuring scattered or reflected electromagnetic radiation, the phase difference and the demodulation factor will provide information about the absorption and reflection characteristics of the target tissue. If the detector 56 is measuring fluorescent radiation emitted by the target tissue, the phase difference and the demodulation factor will provide information about the lifetime and intensity of the fluorescent emissions. In either event, this information can be helpful in determining characteristics of the target tissue. For instance, this information can be used to determine whether a tissue is cancerous or not, the information can be used to distinguish between different types of tissue, and the information can be used to determine chemical properties or the concentrations of various chemicals or ions present in the target tissue.

If the apparatus described above is used to detect fluorescent emissions, the fluorescent emissions can be generated by endogenous or exogenous fluorophores. If the fluorescent material is exogenous, the material may be selected so that it chemically interacts with various compounds in the patient's body. In this instance, the fluorescent lifetime of the exogenous material would vary depending upon the presence or concentration of a compound or ion. As a result, the phase difference value, and/or the demodulation factor m can be used to determine the presence or concentration of the compound or ion. Examples of exogenous fluorescent materials that would be useful in a method as described above are set forth in U.S. Pat. No. 5,624,847 and U.S. Pat. No. 5,628,310, the contents of each of which are hereby incorporated by reference.

Figure 3:
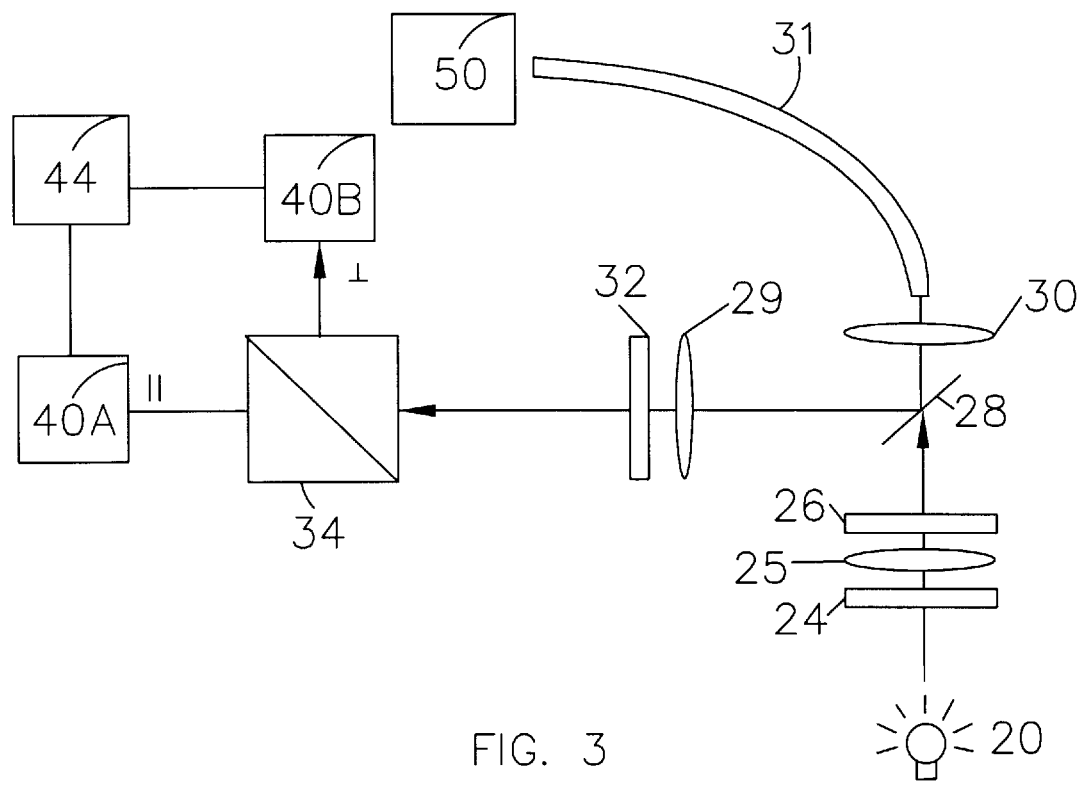
FIG. 3 is a diagram showing an apparatus embodying of the invention capable of performing a polar anisotropy measurement.

A second apparatus and method embodying the invention, which measures fluorescent lifetime via a polarization anisotropy measurement technique, will now be described with reference to FIG. 3. In this measurement technique, a polarized beam of electromagnetic radiation is used to illuminate a target tissue. Components of the fluorophores' excitation dipoles, parallel to the polarization plane of the beam of excitation electromagnetic radiation will then be selectively excited and will emit polarized fluorescent radiation. This emission will have a lifetime that is governed by the physiochemical environment of the fluorophore. Because of Brownian motion, the fluorophores will rotate as they emit radiation. This rotation results in a change in the intensity in each of the emission polarization planes. Brownian rotation in essence provides a time gated window in which to observe the intensity decay due to fluorescence lifetime. By measuring amplitudes of the emitted fluorescent radiation in mutually perpendicular planes, it is possible to determine the lifetime, or decay time, of the fluorescent emissions. This measurement is possible only if the time constant of Brownian rotation, or the rotational correlation time, is not vastly different from the fluorescence lifetime. For most endogenous fluorophores that are indicators of disease this is true. Additionally, exogenous fluorophores can be engineered to satisfy this requirement for applications in disease detection. In a preferred embodiment of the invention, one polarization plane is parallel to the polarization plane of the excitation radiation, and the other is perpendicular to that plane.

This measuring method makes use of the Perrin Equation, which appears below as Equation (6). The Perrin Equation relates fluorescence anisotropy r to the fluorescent lifetime , where $r_0$ is the anisotropy of a molecule in the absence of Brownian motion (the frozen or highly viscous state) and is the rotational (Brownian) correlation time.

$$r_0/r = 1 + \tau/\phi \qquad \text{Equation (6)}$$

Strictly speaking, Equation (6) is only valid for a single exponential decay of both fluorescence lifetime and anisotropy. Single exponential anisotropy decay only occurs for a spherical molecule. Also, for simplicity, the rotational correlation time for a sphere is defined according to Equation (7) below, where $\eta$ is the viscosity, V the volume, R the universal gas constant, and T the absolute temperature.

$$\phi = (\eta V)/(RT) \qquad \text{Equation (7)}$$

Using the above equations and assumptions, it is possible to define the anisotropy factor r according to Equation (8), where $I_l$ is the intensity of fluorescent emissions in a plane parallel to the plane of the excitation electromagnetic radiation, and $I_r$ is the intensity of fluorescent emissions in a plane perpendicular to the plane of the excitation electromagnetic radiation.

$$r = (I_l - I_r)/(I_l + 2I_r) \qquad \text{Equation (8)}$$

An embodiment of the present invention which can measure fluorescent lifetimes, in vivo, by a polarization anisotropy technique will now be described with reference to FIG. 3. In FIG. 3, a source of electromagnetic radiation 20 emits excitation radiation which then passes through a polarizer 24, focusing optics 25, and optionally an emission filter 26. The radiation source 20 can be a laser, a light emitting diode, a fluorescent light tube, an incandescent light bulb, or any other type of light emitting device. In an alternate embodiment, the radiation source 20 and the polarizer 24 could be replaced by a radiation source that emits polarized light.

The polarized and filtered excitation radiation then passes through a dichroic mirror 28, additional focusing optics 30, and one or more optical fibers 31. The polarized excitation radiation exits the optical fibers 31 and illuminates a target tissue 50. Fluorophores in the target tissue 50 will emit fluorescent radiation in response to the excitation electromagnetic radiation. The returned electromagnetic radiation travels back up the optical fiber 31 and through the focusing optics 30. The optical fibers 31 comprise polarization preserving optical fibers such that the polarization of the excitation and return radiation is preserved as the radiation transits the fiber. In other embodiments, one or more emission optical fibers may be used to communicate the excitation radiation to the target tissue 50, and a second group of return optical fibers may be used to communicate the return radiation back to the dichroic mirror 28.

The returned radiation is then reflected by the dichroic mirror 28 through additional optics 29 and, optionally, another filter 32. The returned radiation then enters a polarizing beam splitter 34, which separates the returned electromagnetic radiation into two light beams that are polarized into mutually perpendicular planes. In a preferred embodiment, one polarization plane will be parallel to the polarization plane of the excitation radiation, and the other polarization plane will be perpendicular to that plane. A first one of the separated light beams having a first polarization plane illuminates a first detector 40A. A second of the separated light beams having a second polarization plane that is perpendicular to the first polarization plane illuminates a second detector 40B. The first and second detectors 40A and 40B output signals indicative of the amplitudes of the first and second light beams. The signals from the first and second detectors are then forwarded to a processor 44. The signals from the first and second detectors are used to calculate an anisotropy factor, which provides a measure of the lifetime of the fluorescent emissions. As described above, the fluorescent lifetime can be used to determine various characteristics of the target tissue.

A device or method embodying the present invention, utilizing either the phase shift or the polar anisotropy techniques make it possible to conduct in vivo measurements of tissues on the inside of body passages or lumens. An endoscope embodying the invention can be inserted into a natural body lumen of a patient to search for the presence of cancerous or diseased tissue. This means that no surgery would be required to locate and examine tissues inside the patient's body.

Either the phase shift or the polar anisotropy method may be used to diagnose disease on the inside surfaces of a body lumen or tissues located immediately below the surface. Since the anisotropy detection method relies on polarized light, a reliable measurement of fluorescence lifetime can be made to a depth of several millimeters before losing resolution due to the depolarizing nature of tissue scattering.

Additionally, the phase shift technique is capable of conducting deep tissue measurements of tissues located several centimeters below the surface of a lumen or organ. This diagnosis is possible by either observing the returned scattered excitation radiation or by observing the scattered fluorescence radiation generated by tissue upon interaction with the scattered excitation radiation. Thus, a device embodying the invention that uses the phase shift technique can determine the presence of cancerous or diseased tissue located below or behind the surface of the body lumen or deep within tissue such as in breast or brain tissue.

The above-described methods could be combined to obtain a better or more accurate measure of target tissue characteristics. For instance, a measurement of the phase shift and demodulation factor of reflected/scattered excitation radiation and a measurement of the phase shift and demodulation factor of a fluorescent emission could be used together to obtain a more accurate determination of target tissue characteristics than one measurement alone. A phase shift and demodulation measurement could also be combined with a polar anisotropy measurement.

Similarly, the phase shift and polar anisotropy techniques could be used in conjunction with known intensity based measurement techniques, as described above in the Background of The Invention, to obtain a better determination of target tissue characteristics.

Examples of methods that combine two or more measurement techniques to arrive at a more accurate ultimate determination are given in U.S. Pat. No. 5,582,168 to Samuels, the contents of which are hereby incorporated by reference.

The techniques described above could also be used to map the conditions of an area of target tissue. For instance, any of the above-described techniques could be used to determine a condition of a target tissue adjacent a distal end of a measuring device. The measuring device could then be moved adjacent a different portion of the target tissue, and the measurements could be repeated. This process could be repeated numerous times to determine the conditions of different portions of a target tissue area. The determined conditions could then be used to create a map of the target tissue area, which could be printed or displayed on a monitor.

One of the most difficult problems with in vivo tissue diagnostics and disease measurement is the biological diversity of normal tissue properties between different patients, or even within the same patient. Furthermore, this diversity is time variant both in the long term and in the short term. Long term variations may be due to patient age, hormonal milieu, metabolism, mucosal viscosity, and circulatory and nervous system differences. Short term variations may be from blood perfusion changes due to heart beat, physical movement, local temperature changes etc.

Because of the variability of tissue characteristics, to accurately determine whether a target tissue is diseased, one needs to compare measurements of the target tissue to measurements of normal tissues from the same patient. The measurements of the known normal tissue should be made concurrently or simultaneously with the measurements of the target tissue. The normal tissue measurements then serve as a baseline for normalcy, variations from which may be interpreted as disease. To arrive at a baseline measurement, a number of strategies can be used.

First, visual characteristics such as pigmentations (nevi) in skin, or polyps in the colon, can be used to identify potentially abnormal regions. Normalized or averaged spectra of multiple regions surrounding these potentially abnormal, visually distinct regions can be used to establish baseline measurements. The baseline measurements can then be compared to measurements taken on the abnormal, visually distinct regions. Measurements of normal and abnormal regions based on visual characteristics could be automated using imaging capabilities of the measurement device itself.

In an alternate strategy, measurements can be taken on spaced apart regions along a portion of a lumen or tissue. The spacing between the regions would be dependent on the type of tissue being diagnosed. Then, differentials between individual measurements taken at different regions would be calculated. If differentials are greater than a preset amount, the tissue between the excessively high differentials would be diagnosed as diseased.

In yet another alternate strategy, a gradient in spectral response as one moves away from a visually suspicious site could also be used as a marker for disease. This is easily automated and can be implemented effectively in any imaging modality.

In addition, pattern recognition algorithms (e.g. neural nets) could also be used to analyze differences in readings taken from various sites in the same patient or from multiple readings from different patients.

Figure 4:
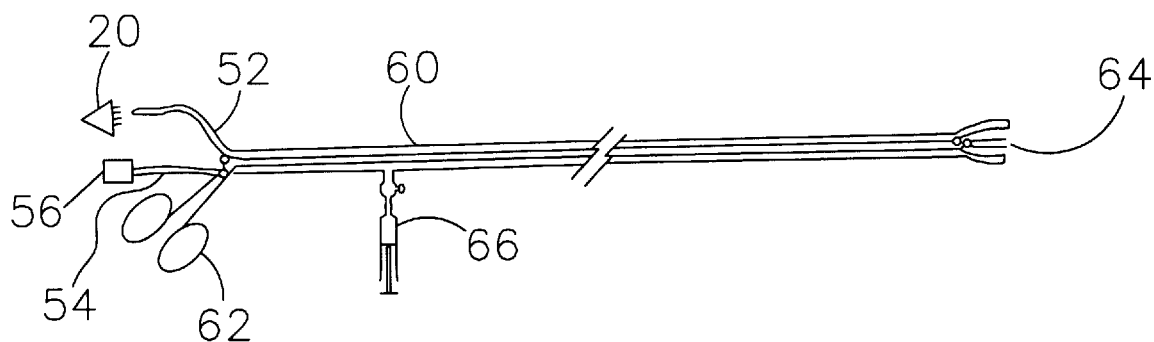
FIG. 4 is a diagram of an endoscope embodying the invention.

FIG. 4 shows an endoscope that could be used to practice any of the above-described measuring techniques. The endoscope 60 includes a transmit optical fiber bundle 52, which can convey excitation electromagnetic radiation from a radiation source 20 to a target tissue. The endoscope 60 also includes a return optical fiber bundle 54 for communicating reflected/scattered electromagnetic radiation or fluorescent emissions from a target tissue to a detector 56. In alternative embodiments, the transmit and return optical fibers could be co-located, or could be the same fibers.

The endoscope 60 may also include a handle 62 for positioning the endoscope, or for operating a device 64 on a distal end of the endoscope 60 intended to remove tissue samples from a patient. The endoscope may also include a device 66 for introducing a dose of medication to a target tissue. Also, the source of electromagnetic radiation 20 may be configured to emit a burst of therapeutic radiation that could be delivered to a target tissue by the endoscope.

Figure 5A:
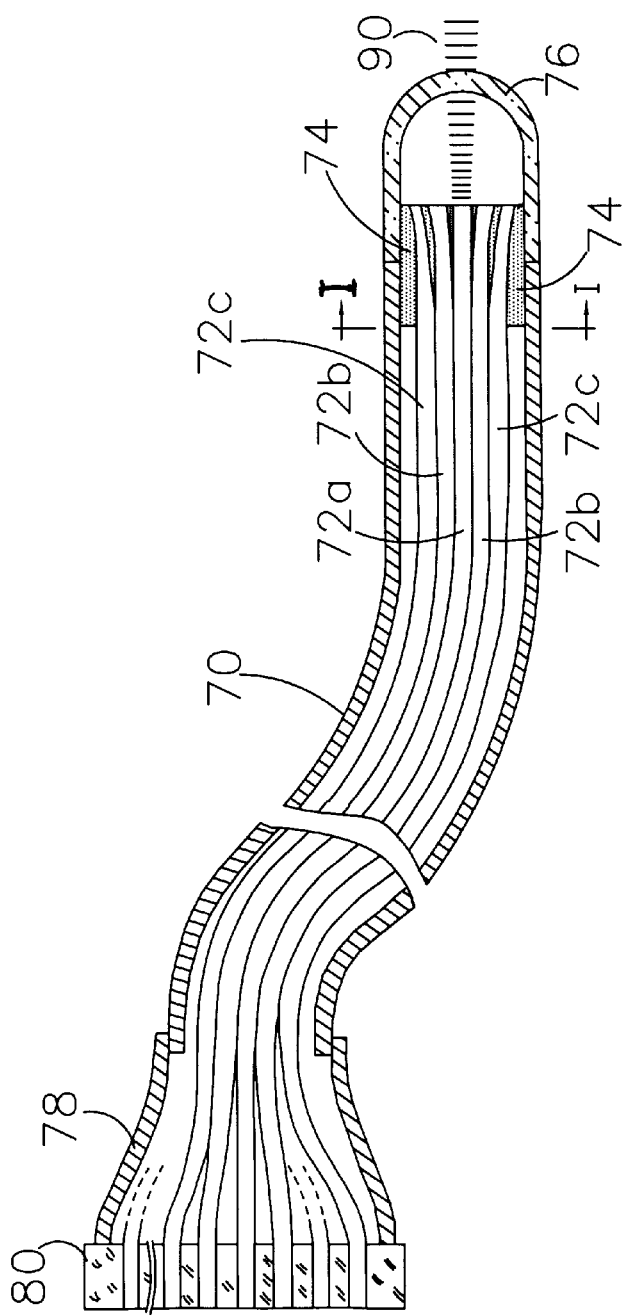
FIGS. 5A and 5B show an embodiment of the invention.
Figure 5B:
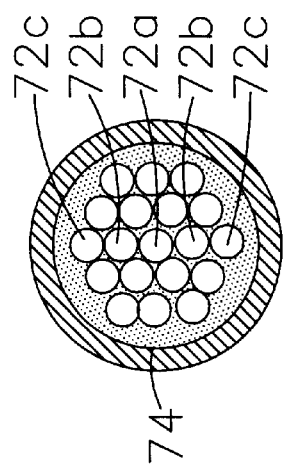

FIGS. 5A and 5B show the structure of an endoscope or catheter which may embody the present invention. The apparatus includes a long body portion 70 which is intended to be inserted into a body of the patient. In the case of a catheter, the body portion 70 must have a diameter sufficiently small to be inserted into blood vessels of the patient. In the case of an endoscope, the body portion of the device 70 must have a diameter that is sufficiently small to be inserted into a natural lumen or body cavity of the patient.

The device includes a proximal end 80, which holds proximal ends of optical fibers 72a–72c. The optical fibers extend down the length of the device and terminate at a distal holding portion 74. The distal holding portion 74 holds the optical fibers in a predetermined orientation. The optical fibers are held such that they can illuminate selected portions of the distal end 76 of the device. This orientation also allows the distal end of the optical fibers to receive radiation from selected areas outside the distal end 76 of the device.

As best seen in FIG. 5B, the optical fibers are arranged such that there is a single central optical fiber 72a surrounded by a first ring of optical fibers 72B, which is in turn surrounded by a second ring of optical fibers 72c. Of course, other orientations of the optical fibers are possible.

By applying excitation electromagnetic radiation to selected ones of the optical fibers, and monitoring the returned electromagnetic radiation through selected ones of the optical fibers, is possible to determine characteristics of target tissues at selected locations outside the distal end of the device. For instance, if the central optical fiber 72*a* emits electromagnetic radiation 90 toward a target tissue, and returned electromagnetic radiation is sensed through the same optical fiber, the returned electromagnetic radiation can be analyzed using any of the above methods to determine characteristics of a target tissue located adjacent the center of the distal end of the device. The same process can be used to determine the condition of a target tissue at different locations around the distal end of the device.

Figure 6A:
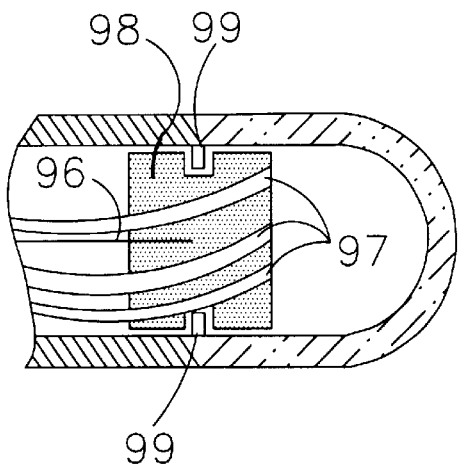
FIGS. 6A, 6B and 6C show the end portions of various embodiments of the invention.
Figure 6B:
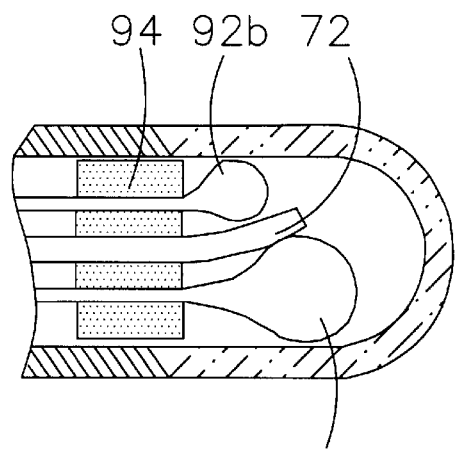
Figure 6C:
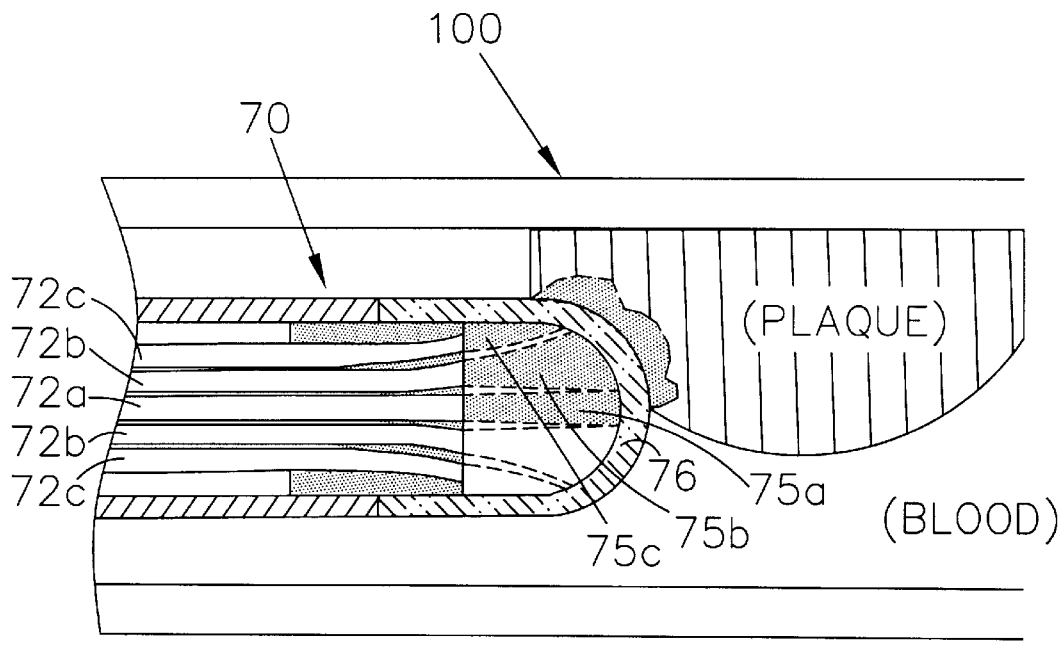

FIGS. 6A–6C show various different distal ends of the device.

In FIG. 6A, the distal ends of the optical fibers are held by a holding portion 98 that aims the distal ends of the optical fibers 97 in a particular direction. A flexible wire or bar 96 is attached to the holding portion 98 and extends to the proximal end of the device. By rotating the flexible wire or bar 96, the holding portion 98 can also be rotated. This allows the distal ends of the optical fibers to be aimed at different portions of the distal end of the device.

FIG. 6B shows another embodiment of the invention that includes one or inflatable balloon portions 92*a*., 92*b*. An optical fiber 72 is located in the center of the device by a holding portion 94. Each of the inflatable balloons 92*a*, 92*b* is also held by the holding portion 94. By selectively inflating or deflating the different balloon portions, the optical fiber 72 may be aimed to illuminate different portions of the distal end of the device or to receive return radiation from selected locations adjacent the distal end of the device.

FIG. 6C shows an embodiment of the device similar to the embodiment shown in FIGS. 5A and 5B. This figure shows how electromagnetic radiation passing down through the optical fibers 72*a*–72*c* can be used to selectively illuminate material or tissue adjacent selected portions of the distal end of the device. In FIG. 6C, only the upper optical fibers are emitting electromagnetic radiation outside the device. This electromagnetic radiation is being used to destroy or atomize plaque which has formed on an inner wall of a blood vessel. By applying electromagnetic radiation to selected ones of the optical fibers, a doctor can carefully remove or correct problems with target tissues or materials.

Figure 7:
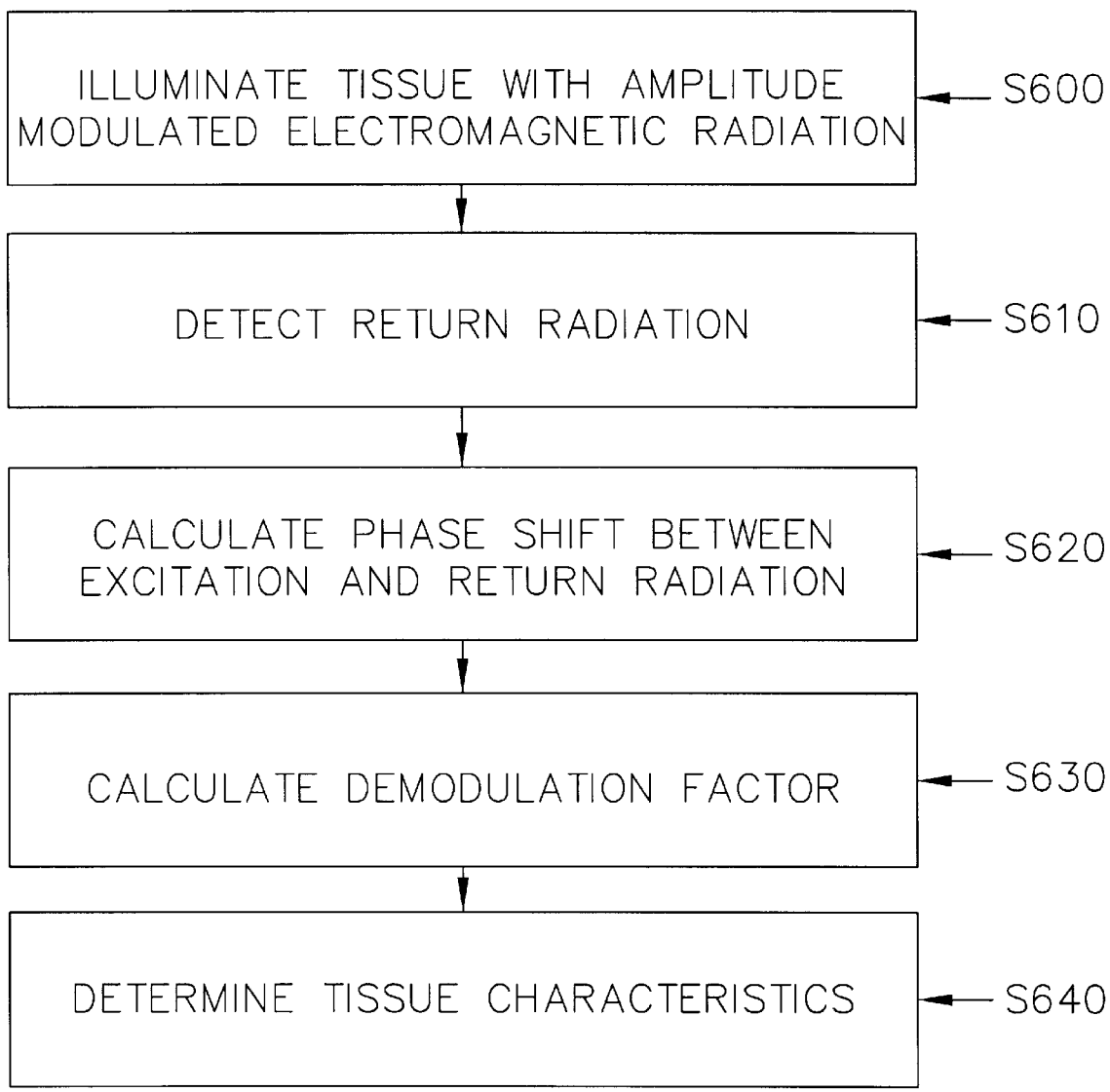
FIG. 7 shows the steps of a method embodying the invention.

FIG. 7 shows steps of a method embodying the invention that can be used to determine the characteristics of a tissue adjacent a device embodying invention. In a first step S600, a target tissue is illuminated with amplitude modulated excitation electromagnetic radiation. In second step S610, returned electromagnetic radiation is detected with a detector. In step S620, a phase shift between the excitation and return electromagnetic radiation is calculated. In another step S630, a demodulation factor representing a ratio of the amplitudes of the excitation and return electromagnetic radiation is calculated. Step S630 is optional but may increase the accuracy of the results. In a final step S640, characteristics of the target tissue are determined based on the calculated phase shift, and optionally the calculated demodulation factor.

Figure 8:
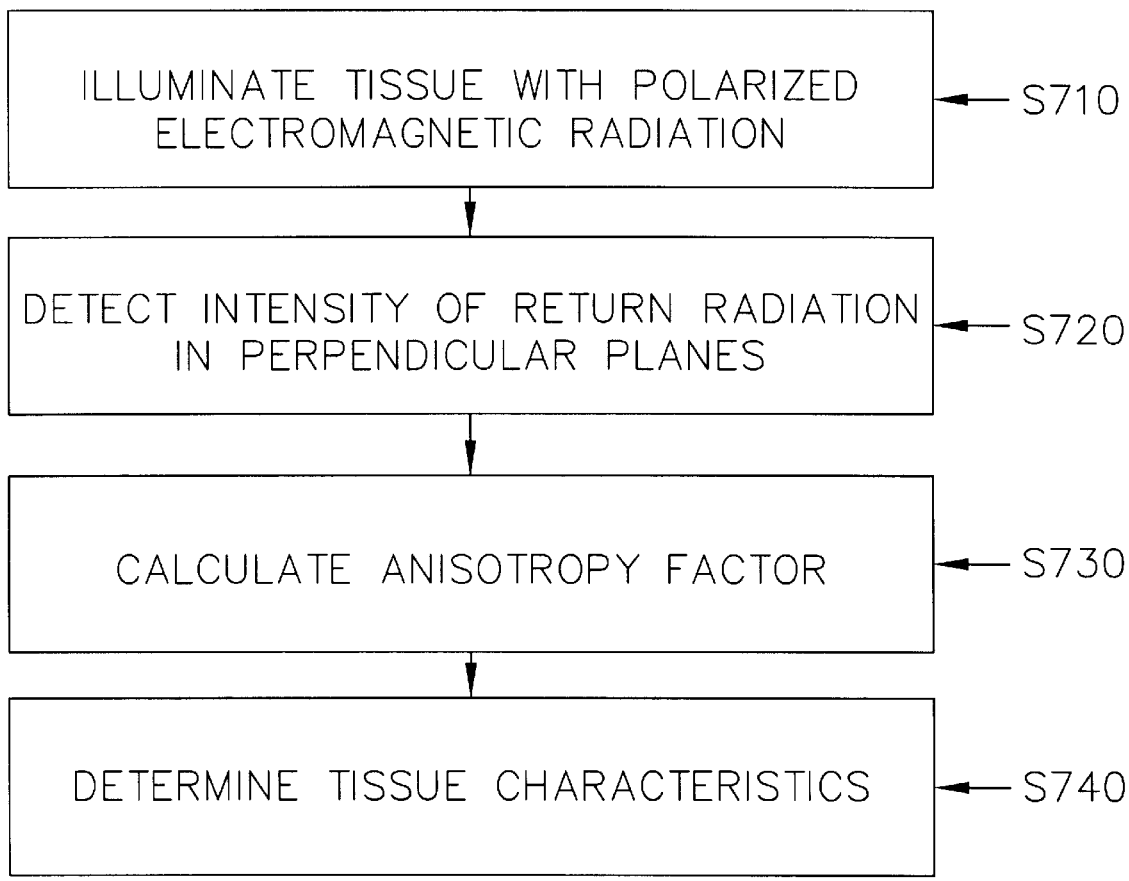
FIG. 8 shows the steps of another method embodying the invention.

FIG. 8 shows another method embodying invention that can be used to determine tissue characteristics. In the first step S710, the target tissue is illuminated with polarized electromagnetic radiation. In the next step S720, the intensity of returned electromagnetic radiation is detected in mutually perpendicular polarization planes. In a preferred embodiment, the amplitude would be detected in planes that are parallel and perpendicular to the polarization plane of the excitation radiation. In the next step S730, an anisotropy factor is calculated based on the detected intensity values for the different polarization planes. In the final step S740, characteristics of a target tissue are determined based on the calculated anisotropy factor.

The foregoing embodiments are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art.

What is claimed is:

1. A method of determining a condition of a target tissue, comprising the steps of:

positioning an instrument adjacent a target tissue of a patient;

conducting a spectroscopic interrogation of the target tissue using a polarization anisotropy based technique, and at least one additional technique selected from the group consisting of an absorption spectroscopic technique, a scattering spectroscopic technique, a steady state fluorescence spectroscopic technique and a time resolved spectroscopic technique, wherein the spectroscopic interrogation comprises taking two measurements at substantially the same location on the target tissue using different techniques; and determining a condition of the target tissue based on the results of the spectroscopic interrogation.

2. The method of claim 1, wherein the conducting step comprises taking the two measurements in a sufficiently short period of time that substantially no biological changes occur at the measured location during the two measurements.

3. The method of claim 2, wherein the step of conducting a spectroscopic interrogation using the at least one additional technique comprises the steps of:

irradiating the target tissue adjacent the instrument with amplitude modulated excitation electromagnetic radiation;

sensing a returned electromagnetic radiation returned from the target tissue; and determining a phase shift between the excitation electromagnetic radiation and the returned electromagnetic radiation.

4. The method of claim 1, wherein the step of sensing a returned electromagnetic radiation comprises sensing a portion of the excitation electromagnetic radiation that is scattered from the target tissue.

5. The method of claim 1, wherein the step of sensing a returned electromagnetic radiation comprises sensing electromagnetic radiation emitted from the target tissue in response to the excitation electromagnetic radiation.

6. The method of claim 1, further comprising a step of determining a demodulation factor representing a ratio of amplitudes of the excitation electromagnetic radiation and the returned electromagnetic radiation.

7. The method of claim 2, wherein the step of conducting a polarization amistropy based spectroscopic interrogation comprises the steps of:

irradiating a target tissue adjacent the instrument with polarized excitation electromagnetic radiation;

sensing a returned electromagnetic radiation that is returned from the target tissue; and determining an anisotropy of the returned electromagnetic radiation.

8. The method of claim 7, wherein the step of determining an anisotropy of the returned electromagnetic radiation comprises determining a first amplitude of the returned electromagnetic radiation in a first polarization plane and determining a second amplitude of the returned electromagnetic radiation in a second polarization plane that is perpendicular to the first polarization plane.

9. The method of claim 8, wherein the step of sensing returned electromagnetic radiation comprises sensing fluorescent radiation emitted from the target tissue in response to the excitation electromagnetic radiation.

10. A method of treating a target tissue, comprising the steps of:

a. positioning an instrument adjacent a target tissue of a patient;

b. conducting a spectroscopic interrogation of the target tissue using a polarization anisotropy based technique, and at least one additional technique selected from the group consisting of an absorption spectroscopic technique, a scattering spectroscopic technique, a steady state fluorescence spectroscopic technique and a time resolved spectroscopic technique, wherein the spectroscopic interrogation comprises taking two measurements at substantially the same location on the target tissue using different techniques; and c. applying a treatment to the target tissue based on the results of step (b).

11. The method of claim 10, wherein the conducting step comprises taking the two measurements in a sufficiently short period of time that substantially no biological changes occur at the measured location during the two measurements.

12. The method of claim 11, wherein the step of conducting a spectroscopic interrogation with at least one additional technique comprises the steps of:

irradiating the target tissue adjacent the instrument with amplitude modulated excitation electromagnetic radiation;

sensing a returned electromagnetic radiation returned from the target tissue;

determining a phase shift between the excitation electromagnetic radiation and the returned electromagnetic radiation; and determining a condition of the target tissue based on the determined phase shift.

13. The method of claim 12, wherein the step of applying a treatment to the target tissue comprises irradiating the target tissue with a therapeutic pulse of electromagnetic radiation.

14. The method of claim 12, wherein the step of applying a treatment to the target tissue comprises applying a therapeutic dose of medication to the target tissue.

15. The method of claim 11, wherein the step of conducting a spectroscopic interrogation using a polarization anisotropy based technique comprises the steps of:

irradiating a target tissue adjacent the instrument with polarized excitation electromagnetic radiation;

sensing a returned electromagnetic radiation returned from the target tissue;

determining an anisotropy of the returned electromagnetic radiation; and determining a condition of the target tissue based on the determined anisotropy.

16. A system for determining a condition of a target tissue of a patient, comprising:

at least one electromagnetic radiation source configured to provide excitation electromagnetic radiation;

at least one coupling device that couples the excitation electromagnetic radiation to a target tissue of a patient;

at least one detecting device that senses returned electromagnetic radiation returned from the target tissue; and a processor configured to determine a condition of the target tissue based on the returned electromagnetic radiation using a polarization anisotropy spectroscopic technique, and at least one additional technique selected from the group consisting of an absorption spectroscopic technique, a scattering spectroscopic technique, a steady state fluorescence spectroscopic technique and a time resolved spectroscopic technique, wherein the system is configured to conduct two measurements using different techniques based on the electromagnetic radiation returned from substantially the same location in the target tissue.

17. The system of claim 16, wherein the system is configured to conduct the two measurements in a sufficiently short period of time that substantially no biological changes occur at the measured location during the two measurements.

18. The system of claim 17, wherein the at least one additional technique comprises a time resolved technique, and wherein:

the at least one electromagnetic radiation source comprises an electromagnetic radiation source for providing modulated excitation electromagnetic radiation; and wherein the processor is configured to determine a phase shift between the excitation electromagnetic radiation and the returned electromagnetic radiation.

19. The device of claim 18, wherein the electromagnetic radiation source for providing modulated excitation electromagnetic radiation comprises an electromagnetic radiation source that provides electromagnetic radiation having an amplitude that varies at a substantially constant frequency.

20. The device of claim 17, wherein the at least one detecting device comprises a device configured to sense fluorescent radiation emitted by endogenous fluorophores of the target tissue in response to the excitation radiation.

21. The device of claim 20, wherein the device comprises a device configured to sense at least a portion of the excitation electromagnetic radiation that is scattered from the target tissue.

22. The device of claim 20, wherein the processor is also configured to determine a decay time of fluorescent radiation.

23. The device of claim 18, wherein the processor is also configured to determine a condition of the target tissue based on the determined phase shift.

24. The device of claim 23, wherein the processor is also configured to create a map of determined conditions of different portions of a target tissue.

25. The device of claim 18, wherein the processor is also configured to determine a demodulation factor representing a ratio of amplitudes of the excitation electromagnetic radiation and the return electromagnetic radiation.

26. The system of claim 17, wherein:

the at least one electromagnetic radiation source comprises an electromagnetic radiation source configured to providing polarized excitation electromagnetic radiation; and the processor is configured to determine an anisotropy of the returned electromagnetic radiation.

27. The device of claim 26, wherein the at least one detecting device comprises a device configured to sense fluorescent radiation emitted from endogenous fluorophores in the target tissue.

28. The device of claim 27, wherein the processor is configured to determine a decay time of the fluorescent radiation based on the determined anisotropy.

29. The device of claim 26, wherein the processor is configured to determine an anisotropy based on a first amplitude of the returned electromagnetic radiation in a first polarization plane and a second amplitude of the returned electromagnetic radiation in a second polarization plane.

30. The device of claim 26, wherein the processor is also configured to determine a condition of the target tissue based on the determined anisotropy.

31. The device of claim 26, wherein the processor is configured to recorded determined conditions of a plurality of different areas of the target tissue, and wherein the processor is configured to create a map of the determined conditions.

32. A method of mapping a target tissue area, comprising the steps of:
  a. contacting a target tissue area of a patient with a measuring instrument;
  b. conducting a spectroscopic interrogation of the target tissue area with the instrument using a polarization anisotropy based technique and at least one additional technique selected from the group consisting of an absorption spectroscopic technique, a scattering spectroscopic technique, a steady state fluorescence spectroscopic technique and a time resolved spectroscopic technique, wherein two measurements are conducted on substantially the same location of the target tissue using different techniques in a sufficiently short period of time that substantially no biological changes occur at the measured location during the two measurements; and
  c. repeating step (b) until all desired locations within the target tissue area have been interrogated.

33. The method of claim 32, wherein the at least one additional technique is a phase shift technique, and wherein the step of conducting a spectroscopic interrogation comprises the steps of:
  irradiating a portion of the target tissue with amplitude modulated excitation electromagnetic radiation;
  sensing a returned electromagnetic radiation returned from the target tissue; and
  determining a phase shift between the excitation electromagnetic radiation and the returned electromagnetic radiation.

34. The method of claim 33, wherein the step of conducting a spectroscopic interrogation further comprises a step of determining a condition of the irradiated portion of the target tissue based on the determined phase shift.

35. The method of claim 34, wherein the step of conducting a spectoscopic interrogation further comprises a step of identifying visual characteristics of the target tissue, and wherein the step of determining a condition of the irradiated portion of the target tissue comprises utilizing the identified visual characteristics of the targettissue to determine a condition of the irradiated portion of the target tissue.

36. The method pf claim 33, further comprising the step of comparing determined phase shifts for different portions of the target tissue area to identify a potentially abnormal portion of the target tissue.

37. The method of claim 36, wherein the comparing step comprises calculating differences between the determined phase shifts.

38. The method of claim 36, wherein the comparing step comprises determining a gradient in the determined phase shifts.

39. The method of claim 33, further comprising a step of generating a map of the conditions of different portions of the target tissue based on the determined phase shifts.

40. The method of claim 39, further comprising the step of conducting a pattern recognition process to determine whether a pattern of conditions exists within the target tissue.

41. The method of claim 32, wherein the step of conducting a spectroscopic interrogation of the target tissue comprises the steps of:
  irradiating the target tissue with polarized excitation electromagnetic radiation;
  sensing a returned electromagnetic radiation that is returned from the target tissue; and
  determining an anisotropy of the returned electromagnetic radiation.

42. The method of claim 41, wherein the step of conducting a spectroscopic interrogation further comprises a step of determining a condition of the target tissue based on the determined anisotopy.

43. The method of claim 42, further comprising a step of generating a map of the conditions of different portions of the target tissue.

44. The method of claim 32, wherein step (b) comprises the steps of:
  conducting a first set of measurements at a first plurality of locations using a first measurement technique; and
  conducting a second set of measurements at the first plurality of locations using a second measurement technique, wherein the first set of measurements and the second set of measurements are conducted in a sufficiently short period of time that no significant biological changes occur in the target tissue while the first and second sets of measurements are conducted.

45. The method of claim 44, wherein step (c) comprises the steps of:
  conducting a first set of measurements at a second plurality of locations using a first measurement technique; and
  conducting a second set of measurements at the second plurality of locations using a second measurement technique, wherein the first set of measurements and the second set of measurements are conducted at the second plurality of locations in a sufficiently short period of time that no significant biological changes occur in the target tissue while the first and second sets of measurements are conducted.

46. A method of mapping a target tissue area, comprising the steps of:
  a. conducting a spectroscopic interrogation of multiple locations within the target tissue area with an instrument using a polarization anisotropy technique and at least one additional technique selected from the group consisting of an absorption spectroscopic technique, a scattering spectroscopic technique, a steady state fluorescence spectroscopic technique and a time resolved spectroscopic technique; and
  b. comparing the interrogation results for different ones of the multiple locations to determine potentially diseased locations within the target tissue area.

47. The method of claim 46, wherein the multiple locations within the target tissue area are all interrogated within a sufficiently short period of time that substantially no biological changes occur in the target tissue area during the interrogation step.

48. The method of claim 46, wherein step (a) comprises conducting two measurements at each of the multiple locations using different measurement techniques, and wherein the two measurements are conducted within a sufficiently short period of time that substantially no biological changes occur in the target tissue area while the two measurements are conducted.

* * * * *